(12) United States Patent
Valentine et al.

(10) Patent No.: US 7,618,423 B1
(45) Date of Patent: Nov. 17, 2009

(54) SYSTEM AND METHOD FOR PERFORMING SPINAL FUSION

(75) Inventors: Keith Valentine, San Diego, CA (US); Pat Miles, San Diego, CA (US); Jared Aramabula, San Diego, CA (US); Jeff Castleberry, Escondido, CA (US); Bryan D. Hildebrand, White Fish, MT (US); Scot Martinelli, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 192 days.

(21) Appl. No.: 10/461,915

(22) Filed: Jun. 14, 2003

Related U.S. Application Data (60) Provisional application No. 60/389,232, filed on Jun. 15, 2002.

(51) Int. Cl.
*A61B 17/58* (2006.01)
(52) U.S. Cl. .......... 606/99
(58) Field of Classification Search .......... 606/86, 606/90, 99, 104, 86 R, 86 A; 623/17.11–17.16
See application file for complete search history.

(56) References Cited

U.S. PATENT DOCUMENTS

| | | | |
|---|---|---|---|
| 3,486,505 A | 12/1969 | Morrison | |
| 3,518,993 A | 7/1970 | Blake | |
| 3,604,487 A | 9/1971 | Gilbert | |
| 3,745,995 A | 7/1973 | Kraus | |
| 3,848,601 A | 11/1974 | Ma et al. | |
| 4,026,304 A | 5/1977 | Levy | |
| 4,026,305 A | 5/1977 | Brownlee et al. | |
| 4,646,738 A | 3/1987 | Trott | |
| 4,657,550 A | 4/1987 | Daher | |
| 4,743,256 A | 5/1988 | Brantigan | |
| 4,781,591 A | 11/1988 | Allen | |
| 4,834,757 A | 5/1989 | Brantigan | |
| 4,877,020 A | 10/1989 | Vich | |
| 4,878,915 A | 11/1989 | Brantigan | |
| 4,932,975 A | 6/1990 | Main et al. | |
| 4,961,740 A | 10/1990 | Ray et al. | |
| 4,962,766 A | 10/1990 | Herzon | |

(Continued)

FOREIGN PATENT DOCUMENTS

CA 2015507 1/1991

(Continued)

OTHER PUBLICATIONS

Alleyne, Cargill H., et al., "Current and future approaches to lumbar disc surgery: A literature review", *Medscape Orthopedics & Sports Medicine*, 1, [www.medscape.com/Medscape/OrthoSportsMed/1997/v01.n11/.../mos3057],(1997).

(Continued)

*Primary Examiner*—Thomas C Barrett
*Assistant Examiner*—Michael J Araj
(74) *Attorney, Agent, or Firm*—Jonathan D. Spangler (57) ABSTRACT

A system and associated methods for performing spinal fusion, involving the use of a graft holder assembly, a locking assembly, and a pair of bone graft implants to simultaneously introduce the bone graft implants into a disc space to thereafter effect spinal fusion.

10 Claims, 7 Drawing Sheets

U.S. PATENT DOCUMENTS

| | | | |
|---|---|---|---|
| 5,026,373 A | 6/1991 | Ray et al. |
| 5,055,104 A | 10/1991 | Ray |
| 5,062,845 A | 11/1991 | Kuslich et al. |
| 5,092,572 A | 3/1992 | Litwak et al. |
| 5,133,717 A | 7/1992 | Chopin |
| 5,133,755 A | 7/1992 | Brekke |
| 5,171,278 A | 12/1992 | Pisharodi |
| 5,192,327 A | 3/1993 | Brantigan |
| 5,217,497 A | 6/1993 | Mehdian |
| 5,269,785 A | 12/1993 | Bonutti |
| 5,284,153 A | 2/1994 | Raymond et al. |
| 5,290,494 A | 3/1994 | Coombes et al. |
| 5,300,076 A | 4/1994 | Leriche |
| 5,304,210 A | 4/1994 | Crook |
| 5,306,307 A | 4/1994 | Senter et al. |
| 5,306,309 A | 4/1994 | Wagner et al. |
| 5,322,505 A | 6/1994 | Krause et al. |
| 5,334,205 A | 8/1994 | Cain |
| 5,336,223 A | 8/1994 | Rogers |
| 5,364,400 A | 11/1994 | Rego, Jr. et al. |
| 5,395,372 A | 3/1995 | Holt et al. |
| 5,397,363 A | 3/1995 | Gelbard |
| 5,405,391 A | 4/1995 | Henderson et al. |
| 5,413,602 A | 5/1995 | Metz-Stavenhagen |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen et al. |
| 5,445,639 A | 8/1995 | Kuslich et al. |
| 5,454,811 A | 10/1995 | Huebner |
| 5,458,638 A | 10/1995 | Kuslich et al. |
| 5,484,403 A | 1/1996 | Yoakum et al. |
| 5,489,308 A | 2/1996 | Kuslich et al. |
| 5,522,879 A | 6/1996 | Scopelianos |
| 5,522,899 A | 6/1996 | Michelson |
| 5,524,624 A | 6/1996 | Tepper et al. |
| 5,527,312 A | 6/1996 | Ray |
| 5,534,030 A | 7/1996 | Navarro et al. |
| 5,540,688 A | 7/1996 | Navas |
| 5,545,222 A | 8/1996 | Bonutti |
| 5,562,736 A | 10/1996 | Ray et al. |
| 5,565,005 A | 10/1996 | Erickson et al. |
| 5,571,190 A | 11/1996 | Ulrich |
| 5,571,192 A | 11/1996 | Schonhoffer |
| 5,593,409 A | 1/1997 | Michelson |
| 5,609,636 A | 3/1997 | Kohrs et al. |
| 5,611,800 A | 3/1997 | Davis et al. |
| 5,611,810 A | 3/1997 | Arnold et al. |
| 5,632,747 A | 5/1997 | Scarborough et al. |
| 5,645,598 A | 7/1997 | Brosnahan et al. |
| 5,653,761 A | 8/1997 | Pisharodi |
| 5,653,762 A | 8/1997 | Pisharodi |
| 5,658,336 A | 8/1997 | Pisharodi |
| 5,658,337 A | 8/1997 | Kohrs et al. |
| 5,662,710 A | 9/1997 | Bonutti |
| 5,665,122 A | 9/1997 | Kambin |
| 5,669,909 A | 9/1997 | Zdeblick et al. |
| 5,676,703 A | 10/1997 | Gelbard |
| 5,683,394 A | 11/1997 | Rinner |
| 5,683,400 A | 11/1997 | McGuire |
| 5,683,464 A | 11/1997 | Wagner et al. |
| 5,690,629 A | 11/1997 | Asher et al. |
| 5,700,264 A | 12/1997 | Zucherman et al. |
| 5,700,291 A | 12/1997 | Kuslich et al. |
| 5,700,292 A | 12/1997 | Marguiles |
| 5,702,449 A | 12/1997 | McKay |
| 5,702,451 A | 12/1997 | Biedermann et al. |
| 5,702,453 A | 12/1997 | Rabbe et al. |
| 5,702,454 A | 12/1997 | Baumgartner |
| 5,702,455 A | 12/1997 | Saggar |
| 5,703,451 A | 12/1997 | Yamamichi et al. |
| 5,707,373 A | 1/1998 | Sevrain et al. |
| 5,711,957 A | 1/1998 | Patat et al. |
| 5,716,415 A | 2/1998 | Steffee |
| 5,720,748 A | 2/1998 | Kuslich et al. |
| 5,720,751 A | 2/1998 | Jackson |
| 5,741,261 A | 4/1998 | Moskovitz et al. |
| 5,755,797 A | 5/1998 | Baumgartner |
| 5,766,252 A | 6/1998 | Henry et al. |
| 5,772,661 A | 6/1998 | Michelson |
| 5,775,331 A | 7/1998 | Raymond et al. |
| 5,779,642 A | 7/1998 | Nightengale |
| 5,782,830 A | 7/1998 | Farris |
| 5,782,919 A | 7/1998 | Zdeblick et al. |
| 5,785,710 A | 7/1998 | Michelson |
| 5,797,909 A | 8/1998 | Michelson |
| 5,800,549 A | 9/1998 | Bao et al. |
| 5,800,550 A | 9/1998 | Sertich |
| 5,814,084 A | 9/1998 | Grivas et al. |
| 5,851,208 A | 12/1998 | Trott |
| 5,865,845 A | 2/1999 | Thalgott |
| 5,865,848 A | 2/1999 | Baker |
| 5,885,299 A | 3/1999 | Winslow et al. |
| 5,888,219 A | 3/1999 | Bonutti |
| 5,888,224 A | 3/1999 | Beckers et al. |
| 5,893,890 A | 4/1999 | Pisharodi |
| 5,904,719 A | 5/1999 | Errico et al. |
| 5,910,315 A | 6/1999 | Stevenson et al. |
| 5,954,769 A | 9/1999 | Rosenlicht |
| 5,968,098 A | 10/1999 | Winslow |
| 5,993,474 A | 11/1999 | Ouchi |
| 6,004,326 A | 12/1999 | Castro et al. |
| 6,015,436 A | 1/2000 | Schunhuffer |
| 6,033,405 A | 3/2000 | Winslow et al. |
| 6,039,761 A | 3/2000 | Li et al. |
| 6,042,582 A | 3/2000 | Ray |
| 6,045,580 A | 4/2000 | Scarborough et al. |
| 6,048,342 A | 4/2000 | Zucherman et al. |
| 6,063,088 A | 5/2000 | Winslow |
| 6,083,225 A | 7/2000 | Winslow et al. |
| 6,096,080 A | 8/2000 | Nicholson et al. |
| 6,102,948 A | 8/2000 | Brosnahan, III |
| 6,120,506 A | 9/2000 | Kohrs et al. |
| 6,132,472 A | 10/2000 | Bonutti |
| 6,159,211 A | 12/2000 | Boriani et al. |
| 6,159,215 A | 12/2000 | Urbahns et al. |
| 6,193,756 B1 | 2/2001 | Studer et al. |
| 6,200,347 B1 | 3/2001 | Anderson |
| 6,210,412 B1 * | 4/2001 | Michelson ............... 606/61 |
| 6,224,607 B1 | 5/2001 | Michelson |
| 6,224,631 B1 | 5/2001 | Kohrs |
| 6,241,769 B1 | 6/2001 | Nicholson et al. |
| 6,241,771 B1 | 6/2001 | Gresser et al. |
| 6,251,140 B1 | 6/2001 | Marino et al. |
| 6,258,125 B1 | 7/2001 | Paul et al. |
| 6,277,149 B1 | 8/2001 | Boyle et al. |
| 6,319,257 B1 | 11/2001 | Carignan et al. |
| 6,371,989 B1 | 4/2002 | Chauvin et al. |
| 6,440,142 B1 | 8/2002 | Ralph et al. |
| 6,442,814 B1 | 9/2002 | Landry et al. |
| 6,454,806 B1 | 9/2002 | Cohen et al. |
| 6,527,773 B1 | 3/2003 | Lin et al. |
| 6,595,998 B2 | 7/2003 | Johnson et al. |
| 6,635,086 B2 | 10/2003 | Lin |
| 6,648,895 B2 * | 11/2003 | Burkus et al. ............ 606/90 |
| 6,723,096 B1 * | 4/2004 | Dorchak et al. .......... 606/61 |
| 6,923,814 B1 * | 8/2005 | Hildebrand et al. ....... 606/99 |
| 2002/0058950 A1 | 5/2002 | Winterbottom et al. |
| 2003/0105528 A1 | 6/2003 | Shimp et al. |
| 2003/0208203 A1 * | 11/2003 | Lim et al. ................ 606/61 |

FOREIGN PATENT DOCUMENTS

| EP | 369603 | 5/1990 |

| | | |
|---|---|---|
| EP | 517030 | 5/1992 |
| EP | 667127 | 8/1995 |
| EP | 706876 | 4/1996 |
| EP | 716840 | 6/1996 |
| EP | 737448 | 10/1996 |
| EP | 796593 | 9/1997 |
| EP | 880938 | 2/1998 |
| EP | 809974 | 4/1998 |
| EP | 809975 | 4/1998 |
| EP | 811356 | 4/1998 |
| WO | WO 91/06261 | 5/1991 |
| WO | WO-94/04100 | 3/1994 |
| WO | WO-94/10928 | 5/1994 |
| WO | WO-95/01810 | 1/1995 |
| WO | WO-96/08205 | 3/1996 |
| WO | WO-96/17564 | 3/1996 |
| WO | WO-96/41582 | 12/1996 |
| WO | WO-97/20513 | 6/1997 |
| WO | WO-97/33525 | 9/1997 |
| WO | WO-97/37620 | 10/1997 |
| WO | WO-98/09586 | 3/1998 |
| WO | WO-98/14142 | 4/1998 |
| WO | WO-98/17208 | 4/1998 |
| WO | WO-98/25539 | 6/1998 |
| WO | WO-99/08627 | 2/1999 |
| WO | WO-99/38461 | 8/1999 |
| WO | WO-00/45712 | 8/2000 |
| WO | WO-00/45713 | 8/2000 |
| WO | WO-01/41681 | 6/2001 |
| WO | WO-01/49333 | 7/2001 |

OTHER PUBLICATIONS

Benini, et al., "Undercutting decompression and posterior fusion with translaminar facet screw fixation in degenerative lumbar spinal stenosis: Technique and results", *Neuro-Orthopedics*, (1995),159-172.

Kambin, et al., "History and current status of percutaneous arthroscopic disc surgery", *Spine,* 21, (1996),57S-61S.

Stein, et al., "Percutaneous facet joint fusion: Preliminary experience", *Journal of Vascular and Interventional Radiology*, 4, (1993),69-74.

Vamvanij, et al., "Surgical treatment of internal disc disruption: An outcome study of four fusion techniques", *Journal of Spinal Disorders,* 4, (1998),375-382.

* cited by examiner

SYSTEM AND METHOD FOR PERFORMING SPINAL FUSION

CROSS-REFERENCES TO RELATED APPLICATIONS

The present application is a US Non-Provisional Patent Application of and claims the benefit of priority from commonly owned and co-pending U.S. Provisional Patent Application Ser. No. 60/389,232 (filed Jun. 15, 2002), the entire contents of which is hereby expressly incorporated by reference into this disclosure as if set forth fully herein.

BACKGROUND OF THE INVENTION

I. Field of the Invention

The present invention relates to medical devices and methods generally aimed at spinal surgery. In particular, the disclosed system and associated method relate to performing spinal fusion.

II. Discussion of the Prior Art

Spinal discs serve to cushion and stabilize the spine in addition to distributing stress and damping cyclic loads. The discs may become damaged due to injury or age and symptoms of a damaged disc may include severe pain, numbness or muscle weakness. Fusion is one method of reducing the magnitude of the symptoms of damaged spinal discs. The primary goal of spinal fusion is to restore disc height and provide stability between adjacent vertebrae while promoting the formation of an osseous bridge between the adjacent vertebrae (so called "bony fusion"). Materials are often used in conjunction with the various stabilization devices to encourage bony fusion. Forming an osseous bridge requires osteogenic cells, an adequate blood supply, sufficient inflammatory response, preparation of the local bone to expose cancellous bone and a high quality graft material. The graft material must be conducive to the creeping substitution of bone and may be included within implants or used to construct the implants. Autograft and allograft bone are examples of materials conducive to natural bony fusion that are used to create bone implants.

Bone allograft implants have experienced proliferated use over time. A problem exists, however, in that cadaveric bone (used to produce bone allograft implants) is oftentimes of insufficient dimension to produce grafts of adequate height, especially in cervical applications. More specifically, the femur thickness (that is, the distance between the outer surface of the femur and the inner surface of the intermedullary canal) reduces with age. Therefore, as the donor pool ages, the thickness of donated femurs decreases. In the field of allograft processing, industry practice favors using this "femur thickness" dimension as the height of the resulting cervical allograft. However, the general reduction in the "femur thickness" dimension attributable to age effectively limits and creates a general shortage in the amount of cadaveric bone that can be used in such cervical applications because it is of insufficient dimension to restore disk height.

Efforts to overcome the size limitation have been undertaken (such as providing bone implants formed from multiple laminations), but have failed or are lacking in various respects. The shortcomings of the prior art coupled with the bone shortage have created the need for a system that is structurally improved while being adapted to the allograft bone that is available.

The present invention is directed at addressing this need and eliminating, or at least reducing, the effects of the shortcomings of the prior art systems as described above.

SUMMARY OF THE INVENTION

The present invention discloses a system and method for the simultaneous insertion of multiple bone implants into an intervertebral space. The system includes an insertion tool capable of releasably securing at least two bone implants during insertion into the disk space and thereafter releasing the bone implants in a predetermined configuration to effect fusion over time. The insertion tool includes (by way of example only) a graft holder assembly for holding the grafts and a locking assembly for locking and unlocking the grafts within the holder assembly. The bone implants may thus be simultaneously introduced into a disc space (while locked within the holder assembly) and thereafter released (by disengaging the locking assembly) to restore and maintain adequate disk height. While described herein primarily with reference to the cervical spine, it is to be readily appreciated that the system and method of the present invention may be suitable for use to accomplish fusion in any spinal region (lumbar, thoracic, and cervical).

In one aspect of the present invention, the bone implants may be oriented within the insertion tool such that, once inserted, they will automatically be in this same orientation after being left in the disc space. In a still further aspect, the bone implants may be oriented such that their height (H) is greater than their width (W) when disposed within the disc space (with a length (L) being preferably greater than both height H and width W).

By orienting the bone implants in this fashion, the present invention is capable of restoring and maintaining adequate disc height notwithstanding a general shortage of single graft bone implants having sufficient height and strength to effect fusion. That is to say, by placing bone grafts of reduced overall size on their "sides" (with the graft implant rotated approximately 90 degrees such that the dimension that would ordinarily be the width now constitutes the height) they may still be useful. More importantly, the grafts accomplish this without jeopardizing their structural integrity or stability once implanted, since they are disposed a distance from one another so as to provide, in essence, a base or "stance" of increased dimension.

In another aspect of the present invention, various materials may be positioned or introduced between the bone implants before, during, or after they are disposed in the stanced position within the disk space as described above. Such materials may include, but are not necessarily limited to, bone autograft harvested from the patient receiving the grafts of the present invention, one or more additional bone allograft implants, any number of non-bone implants, and any number of fusion promoting compounds (such as bone morphogenic protein).

Inserting two, or more, allograft implants simultaneously creates a sufficient combined area to provide stability and sufficient force distribution to withstand the compressive stresses in the spine. Additionally, the monolithic grafts do not risk the separation of layers possible in implants constructed from multiple laminations. The allograft implants are also conducive to natural fusion, germane to the human body and do not hinder post-operative imaging.

BRIEF DESCRIPTION OF THE DRAWINGS

Other objects and advantages of the invention will become apparent upon reading the following detailed description and upon reference to the drawings in which.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination.

Figure 1:
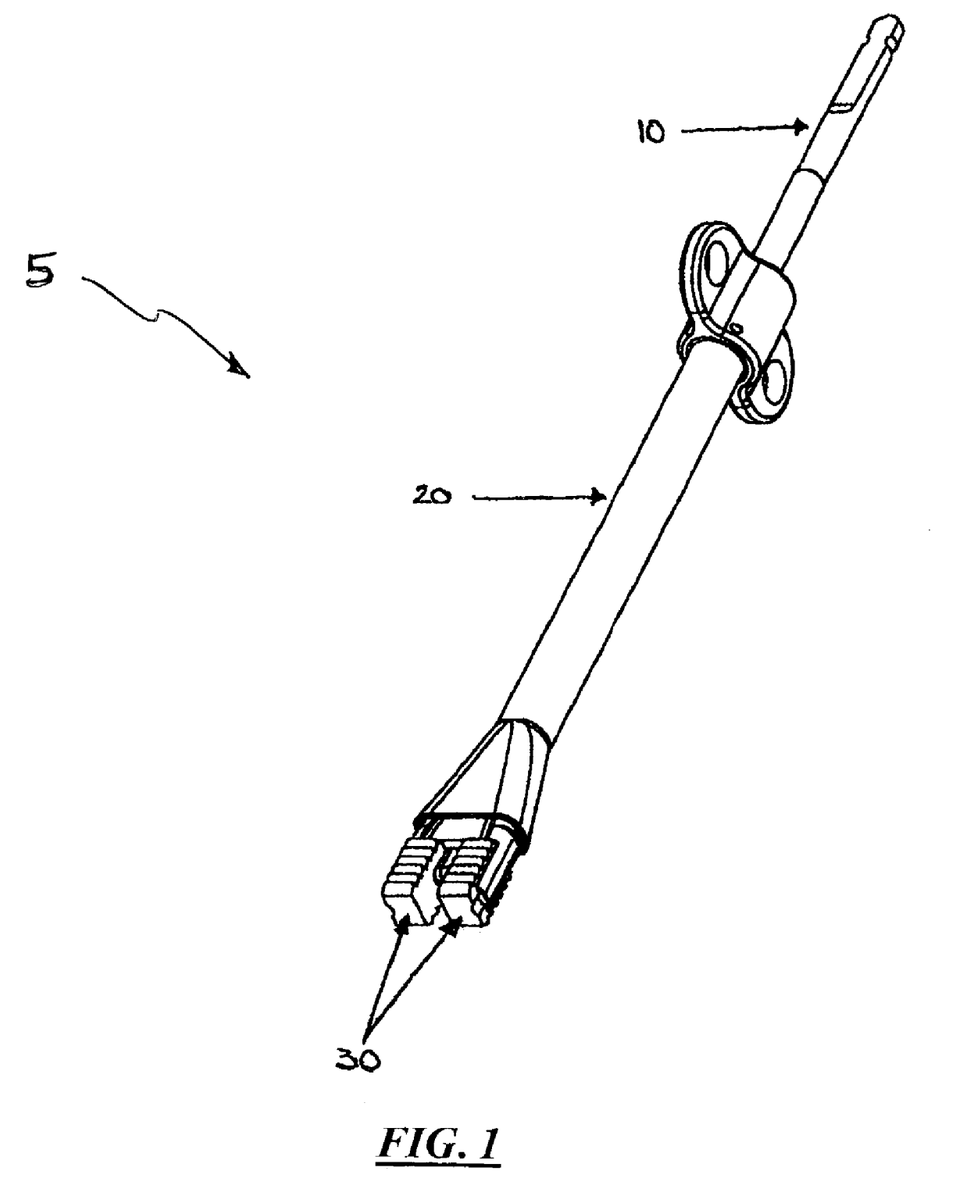
FIG. 1 is a perspective view of the system for performing spinal fusion according to one aspect of the present invention, including a graft holder assembly, a locking assembly, and a pair of bone graft implants.
Figure 2:
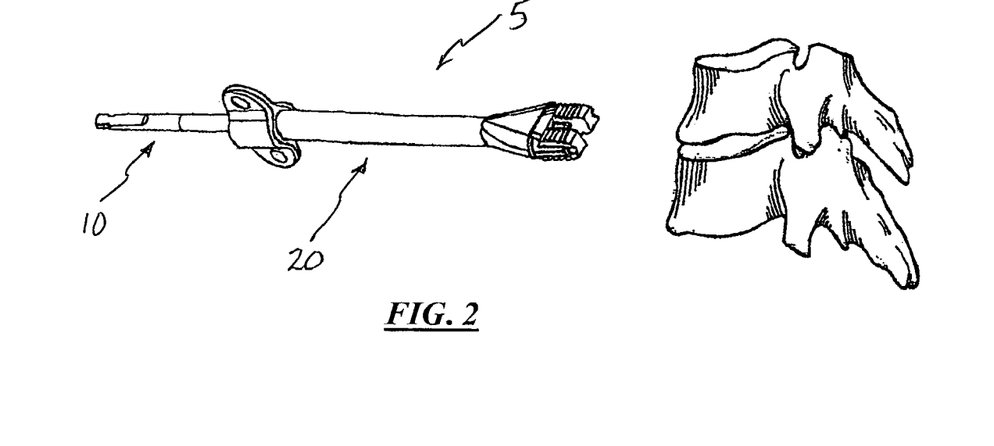
FIGS. 2-4 depict the system of FIG. 1 in use performing spinal fusion according to the present invention.
Figure 3:
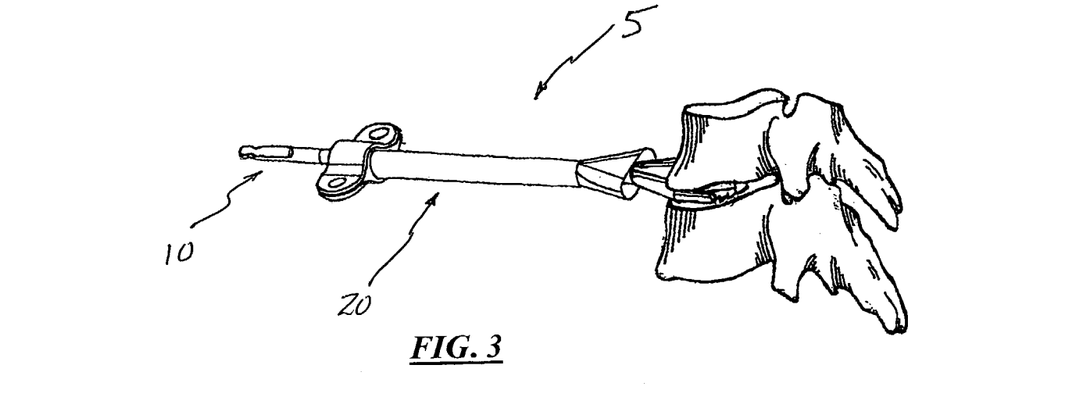
Figure 4:
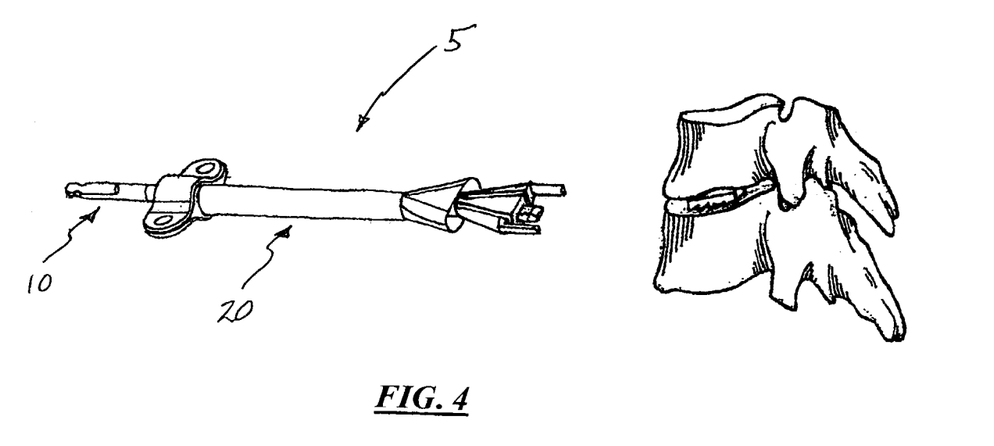

FIG. 1 illustrates a system 5 for performing spinal fusion according to one aspect of the present invention. The system 5 includes a graft holder assembly 10, a locking assembly 20, and a pair of bone graft implants 30. As will be described in detail below, the graft holder assembly 10 and locking assembly 20 cooperate to releasably maintain the bone graft implants 30 in the predetermined "stanced" (or spaced) configuration shown. With brief reference to FIGS. 2-4, the bone graft implants 30 may be simultaneously introduced into a disc space (while locked within the holder assembly 10 as shown in FIG. 2) and thereafter released (by disengaging the locking assembly 20 as shown in FIGS. 3-4). The bone implants 30, having been deposited in the disc space in this "stanced" configuration, effect spinal fusion over time. This fusion may be facilitated or augmented by introducing or positioning various materials between the graft implants 30 (before, during, or after their introduction), such as bone autograft harvested from the patient receiving the grafts 30, one or more additional bone allograft implants, any number of non-bone implants, and any number of fusion promoting compounds (such as bone morphogenic protein). While described below primarily with reference to the cervical spine, it is to be readily appreciated that the system for performing spinal fusion of the present invention may be suitable for use to accomplish fusion in any spinal region (lumbar, thoracic, and cervical).

Figure 5:
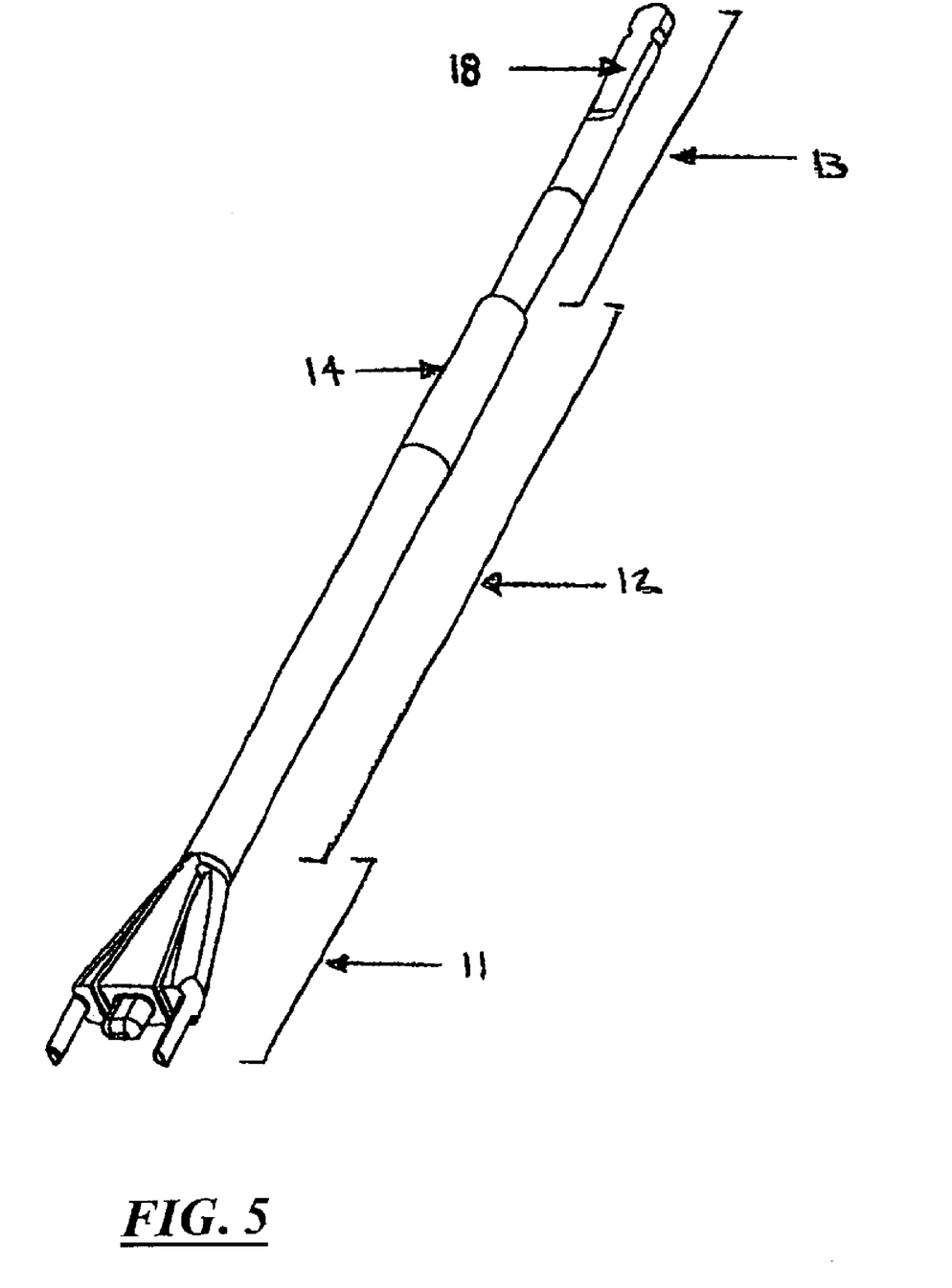
FIG. 5 is a perspective view of a graft holder assembly forming part of the system for performing spinal fusion shown in FIG. 1.
Figure 6:
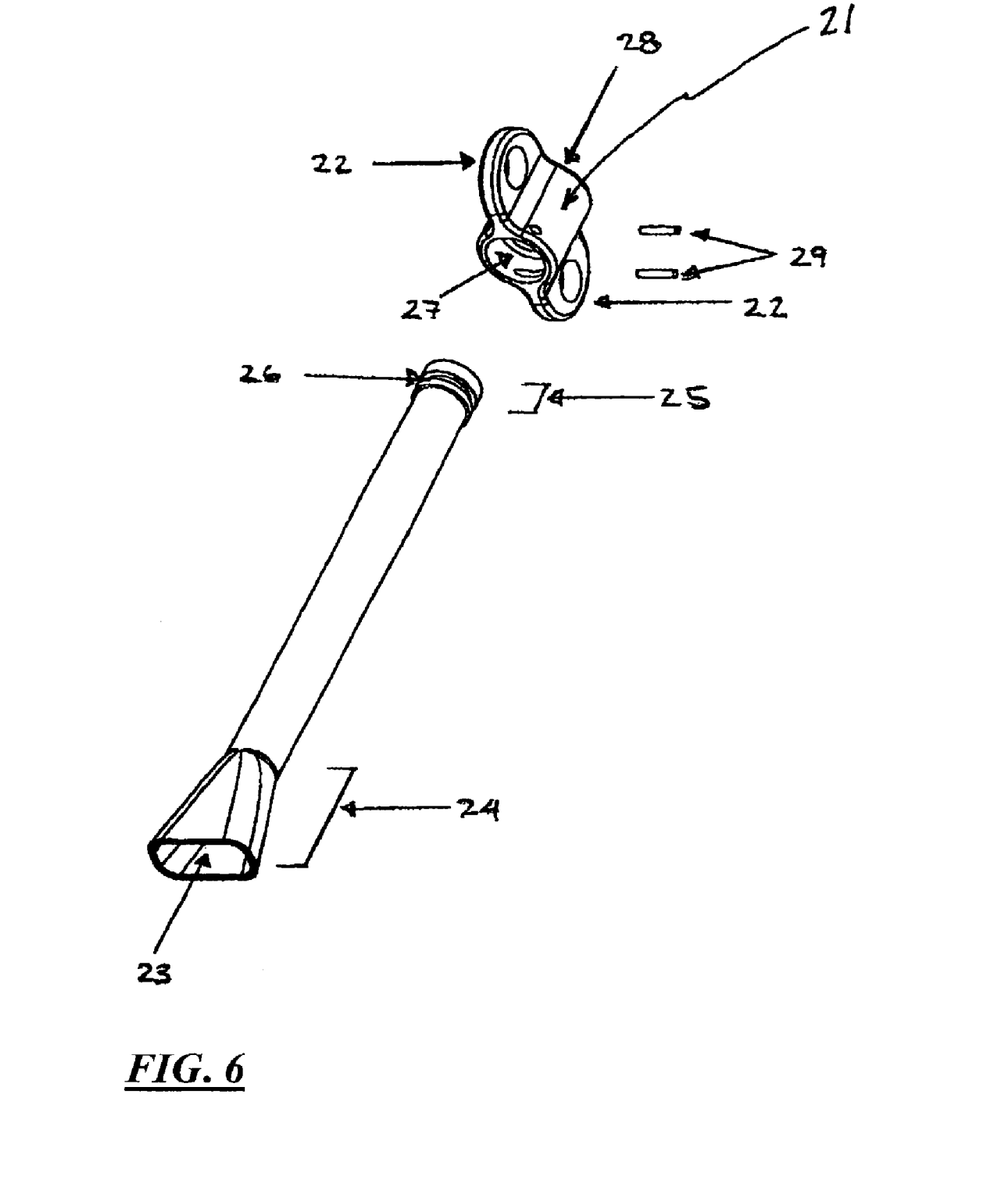
FIG. 6 is a perspective view of a locking assembly 20 forming part of the system for performing spinal fusion shown in FIG. 1.

FIG. 5 details the graft holder assembly 10 of the present invention. The graft holder assembly 10 includes three main functional sections: a clamping section 11, an intermediate section 12, and a handling section 13. The section most proximal on the graft holder assembly 10 is the handling section 13. The handling section 13 in the preferred embodiment is cylindrical with an outer diameter smaller than all other sections, and has at least one flat region 18 for gripping by hand. The function of the handling section 13 is to provide, sufficient area for a surgeon to manipulate the tool during surgery. The intermediate section 12 has two main functions. First, it is used to create the length required to extend from outside the patient's body to the surgical site. It should also preferably provide a manner of engaging or locking the graft holder assembly 10 to the locking assembly 20. By way of example only, this may be accomplished by providing a threaded portion 14 approximately one inch on the proximate end of the intermediate section 12. As will be described in greater detail below, the threaded portion 14 is preferably configured to threadably cooperate with the interior of a locking nut 21 of the locking assembly 20 (FIG. 6). In this manner, the graft holder assembly 10 may be selectively positioned relative to the locking assembly 20 to selectively lock and release the bone graft implants 30.

Figure 7:
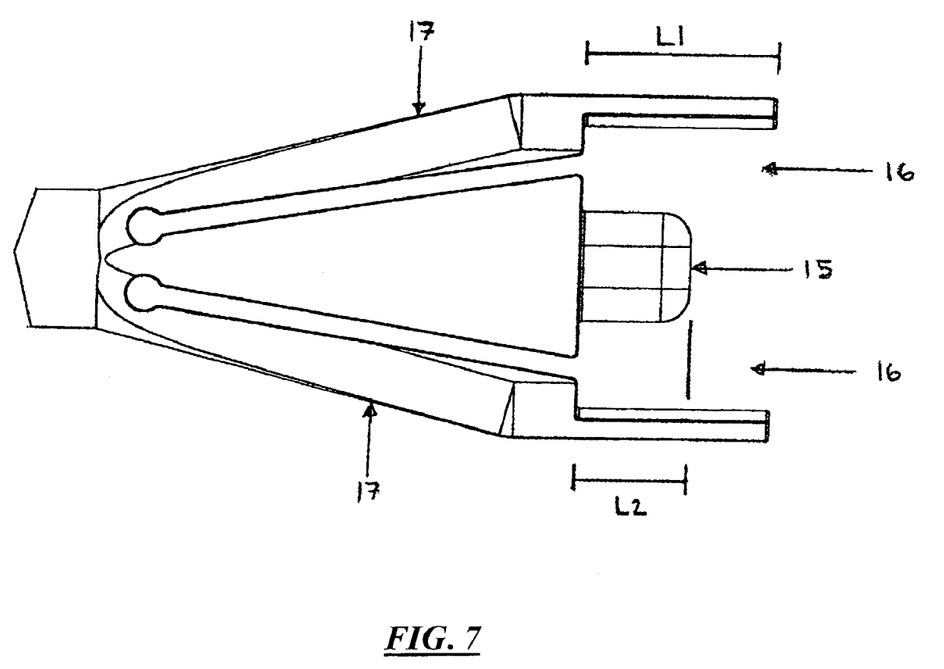
FIG. 7 is an enlarged top view of a clamping section of the graft holder assembly shown in FIG. 5.
Figure 8:
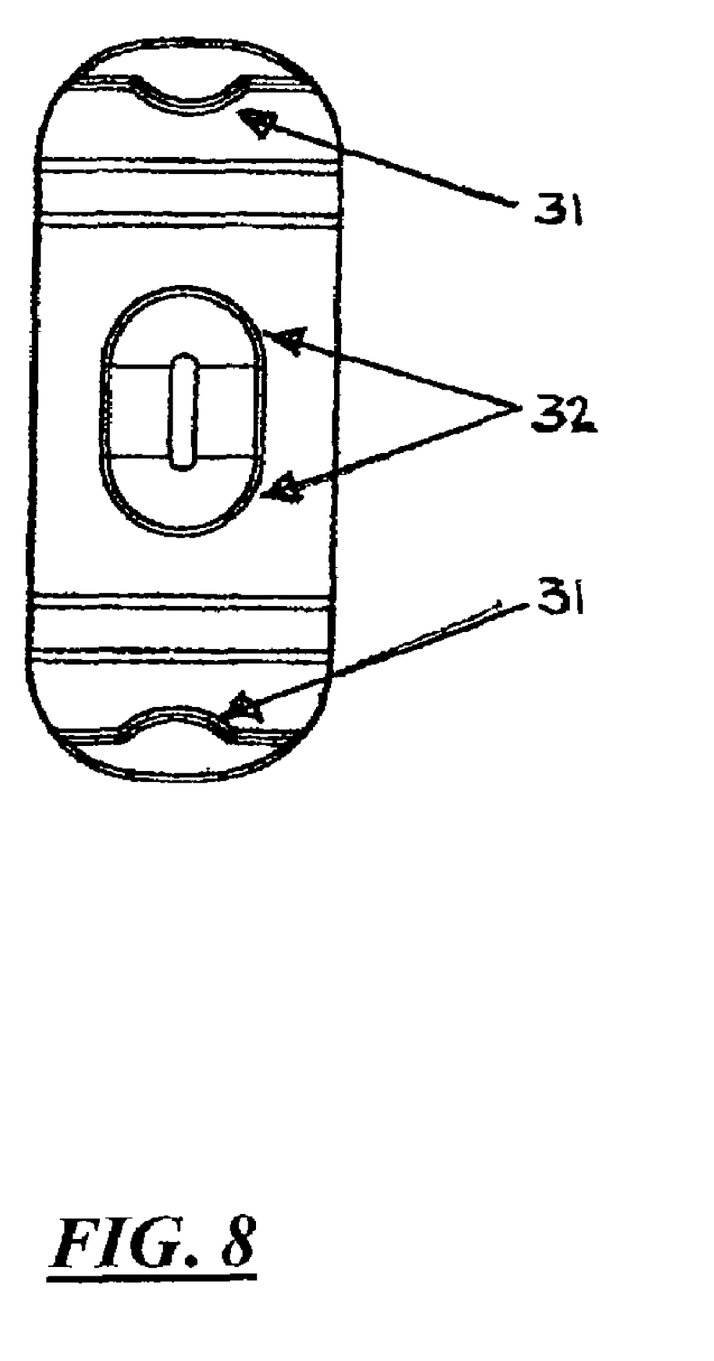
FIG. 8 is an enlarged front view of the clamping section shown in FIG. 7.
Figure 9:
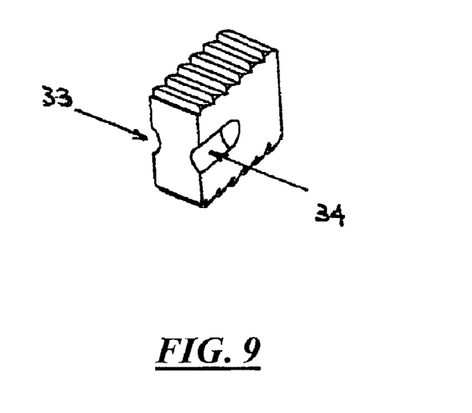
FIGS. 9-10 are perspective views illustrating the opposing sides of a graft employed with the system for performing spinal fusion according to the present invention.
Figure 10:
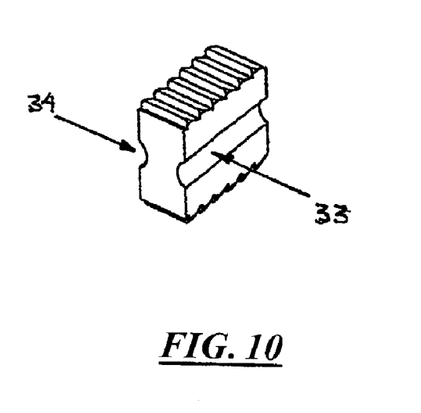
Figure 11:
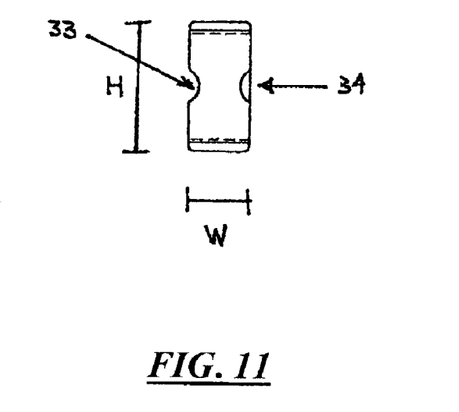
FIGS. 11-12 are end and side views, respectively, of the graft shown in FIGS. 9-10.
Figure 12:
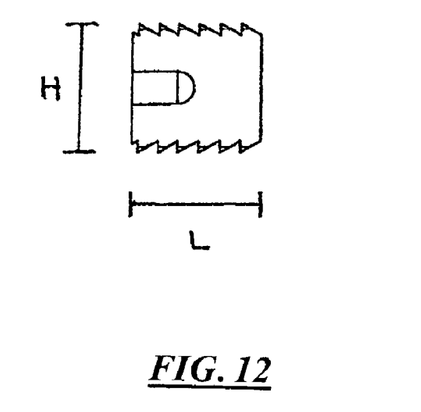

FIGS. 7-8 detail the clamping section 11 of the graft holder assembly 10 of the present invention. Clamping section 11 includes a center support post 15 for spacing and aligning the implants 30 with respect to each other and the graft holder assembly 10. The clamping section 11 provides two clamping regions 16 on its distal end defined by two clamping arms 17 and the center support post 15. The clamping arms 17 extend from the distal end of the clamping section 11 to the proximal end of the clamping section 11 and are substantially parallel to and spaced away from the tapered lateral surfaces of the center support post 15. The clamping arms 17 are attached to the distal end of the intermediate section 12 to allow for lateral bending toward the center support post 15. Engagement surfaces 31, 32 with semi-circular cross-section are disposed on both the clamping arms 17 and the center support post 15 and are used to engage or mate with channels in the sides of the implants 30. The length L2 of the engagement surfaces 32 of the center support post 15 extend only part of the length L1 of the engagement surfaces 31 of the clamping arms 17.

FIG. 6 details the locking assembly 20 of the present invention. The locking assembly 20 includes a central bore 23 dimensioned to receive the graft holder assembly 10 therein. A clamp-receiving portion 24 is provided at the distal end of the locking assembly 20. The clamp-receiving portion 24 is configured to receive the clamping section 11 of the graft holder assembly 10. The width of the clamp-receiving portion 24 of the locking assembly 20 is smaller than the freestanding width of the clamping section 11 of the graft holder assembly 10. As the graft holder assembly 10 is drawn into the locking assembly 20 (via the threaded engagement of the threaded portion 14 and locking nut 21), the clamp-receiving portion 24 of the locking assembly 20 forces the clamp arms 17 to displace laterally toward the center axis of the graft holder assembly 10. This results in application of a compressive force on the implants 30 located between the clamping arms 17 and the center support post 15. The cross-section of the clamp-receiving portion 24 is substantially rectangular to correspond to the cross-section of the clamping section 11 of the graft holder assembly 10.

A sheath collar 25 with a circumferential channel 26 is located on the distal end of the locking assembly 20. The locking nut 21 receives the sheath collar 25 within a proximal collar-receiving bore 27 with a diameter substantially equivalent to the outer diameter of the sheath collar 25. A second concentric bore 28 extends through the locking nut 21 with a diameter smaller than the outer diameter of the collar receiving bore 27. The difference in bore diameters creates a shoulder limiting the distance the sheath collar 25 may be received into the collar-receiving bore 27 of the locking nut 21. Two parallel dowel pins 29 are inserted into the locking nut 21 perpendicular and offset from the central axis of the collar-receiving bore 27 and are received in the circumferential channel 26. The inserted dowel pins 29 restrict axial movement of the locking nut 21 with respect to the remainder of the sheath actuation member while allowing free rotation of the locking nut 21 about the sheath collar 25. The inner surface of the second, smaller bore 28 through the locking nut 21 is threaded to engage the threaded portion 14 of the intermediate section 12 of the graft holder assembly 10.

To ease the rotation of the locking nut 21 by hand, two semi-circular wings 22 may be provided protruding from either side of the locking nut 21. Alternatively, other methods of creating a gripping surface are contemplated including but not limited to knurling or facets. As the locking nut 21 is tightened onto the threaded portion 14 of the graft holder assembly 10, the clamping force imposed upon the implants 30 increases. Conversely, as the locking nut 21 is loosened from the threaded portion 14 of the graft holder assembly 10, the clamping force upon the implants 30 is reduced allowing the device to be removed after the implants 30 are positioned within the intervertebral space, leaving the implants in place.

FIGS. 9-12 detail the bone graft implants 30 of the present invention. Bone graft implants 30 are preferably constructed with channels 33, 34 and cross-section used in conjunction with the system to assure proper orientation of the implants. The channel and engagement surface combination also allows for the precise alignment of the implants in both the lateral and vertical axes. Alternatively, the cross-section of such surfaces may be any shape, including but not limited to rectangular or triangular, to allow the proper alignment and axial freedom of the implants (that is, to allow the grafts to exit the end of the holder assembly 10).

The graft holder assembly 10, locking assembly 20 and graft implants 30 may be provided having any number of suitable sizes and dimensions depending upon the particular spinal level (i.e., lumbar, thoracic, or cervical). By way of example only, for cervical applications, the graft implants 30 have a preferred length L from 8 to 16 millimeters, a preferred width W from 4 to 7 millimeters, and a preferred height H from 5 to 14 millimeters. As illustrated, graft implants 30 are positioned in a manner to perform a single level fusion, however, use of graft implants of height H greater than 14 millimeters are contemplated for use in multi-level fusion procedures (e.g., corpectomy).

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternative falling within the spirit and scope of the invention as defined by the appended claims.

For example, although shown and described above with reference to implants formed from bone, it is to be readily appreciated that the insertion tool and manner of delivering multiple implants simultaneously may be employed with implants of any number of suitable constructions, including but not limited to metal, ceramic, plastic or composite. Moreover, with regard to bone, it will be readily appreciated that this term may be construed to include bone autograft (from the patient), allograft (from other human cadavers), or xenograft (bone from other species).

The invention claimed is:

1. A system for performing spinal fusion, comprising:
   at least two bone implants, each of said bone implants comprising at least one of allograft and autograft bone; and
   an inserter adapted to simultaneously insert said at least two bone implants into a disc space, said inserter including a holder dimensioned to hold said at least two implants, said holder including a spacer post for separating said at least two bone implants by a predetermined distance during insertion and at least two clamping arms for holding said at least two implants in a desired orientation during insertion, said inserter further including a locking assembly including a clamping portion which places pressure on said clamping arms to releasably hold said at least two bone implants, wherein said clamping portion is slidable relative to said holder.

2. The system of claim 1 and further, wherein said locking assembly includes a tubular element and a locking nut coupled to said clamping portion.

3. The system of claim 2 and further, wherein said holder includes an external threaded region, and wherein said locking nut includes internal threads for threadedly engaging with said external threaded region of said holder.

4. The system of claim 1 and further, wherein each bone implant is dimensioned to be releasably engaged between said spacer post and one of said clamping arms.

5. The system of claim 4 and further, wherein each of said at least two bone implants includes a medial groove for engagement with said spacer post, and a lateral groove for engagement with at least one of said clamping arms.

6. A system for simultaneously inserting multiple implants into an intervertebral space to effect spinal fusion, comprising:
   a plurality of bone implants, each of said bone implants comprising at least one of allograft and autograft bone; and
   an inserter adapted to simultaneously deliver said plurality of bone implants into said intervertebral space, said inserter having a holder dimensioned to releasably hold said plurality of bone implants, said holder including a spacer post for separating said plurality of bone implants by a predetermined distance during insertion and at least two clamping arms for holding said plurality of bone implants in a desired orientation during insertion, said inserter further including a locking assembly which cooperates with said clamping arms to releasably hold said plurality of bone implants within said holder.

7. The system of claim 6 and further, wherein said locking assembly includes a clamping portion which places pressure on said clamping arms allowing them to releasably hold said plurality of implants.

8. The system of claim 7 and further, wherein said clamping portion is slidable relative to said holder.

9. The system of claim 8 and further, wherein said locking element includes a tubular element and a locking nut coupled to said clamping portion.

10. The system of claim 9 and further, wherein said holder includes an external threaded region, and wherein said locking nut includes internal threads for threadedly engaging with said external threaded region of said holder.

\* \* \* \* \*